United States Patent

McQueen

Patent Number: 5,207,663
Date of Patent: May 4, 1993

[54] URINARY AND BOWEL INCONTINENCY CONTROL UNDERGARMENT

[75] Inventor: Janet McQueen, Trenton, N.J.

[73] Assignee: McNeil-PPC, Inc., Milltown, N.J.

[21] Appl. No.: 839,051

[22] Filed: Feb. 18, 1992

Related U.S. Application Data

[63] Continuation of Ser. No. 695,166, May 3, 1991, abandoned.

[51] Int. Cl.⁵ .............. A61F 13/15; A61F 13/20; A41B 9/00; A41B 9/08
[52] U.S. Cl. .................. 604/385.1; 604/358; 604/359; 604/360; 604/385.2; 604/395; 604/396; 2/400; 2/406; 2/408
[58] Field of Search ............... 604/358, 385.1, 385.2, 604/395–397, 400, 359, 360; 2/401, 406–408, 400

[56] References Cited

U.S. PATENT DOCUMENTS

| | | | |
|---|---|---|---|
| 2,292,030 | 8/1942 | Kraft | 604/399 |
| 4,368,733 | 1/1983 | Sanidas | 604/327 |
| 4,446,575 | 5/1984 | Davis | 2/408 |
| 4,637,078 | 1/1987 | Southwell | 2/408 |
| 4,695,279 | 9/1987 | Steer | 2/406 |
| 4,892,536 | 1/1990 | Desmarais et al. | 604/385.2 |
| 4,930,161 | 6/1990 | Cohen | 2/408 |
| 4,968,312 | 11/1990 | Khan | 604/385.1 |
| 5,005,525 | 4/1991 | Stanton | 604/385.1 |
| 5,062,840 | 11/1991 | Holt et al. | 604/385.1 |
| 5,106,382 | 4/1992 | Henry | 604/385.1 |

FOREIGN PATENT DOCUMENTS

| | | | |
|---|---|---|---|
| 0359410 | 4/1990 | European Pat. Off. | 604/358 |
| 2561078 | 9/1985 | France | 604/385.1 |

*Primary Examiner*—Randall L. Green
*Assistant Examiner*—Paul Zuttarelli

[57] ABSTRACT

This invention relates to a protective undergarment for an individual who is bowel incontinent. The undergarment provides an elasticized, double panel pouch that is suspended from a waistband whereby the inner panel of the pouch is drawn between the buttocks of the individual. An elasticized slit opening on the inner panel of this pouch is thereby positioned adjacent to the individual's anus and permits the admission of fecal material directly into the pouch.

27 Claims, 2 Drawing Sheets

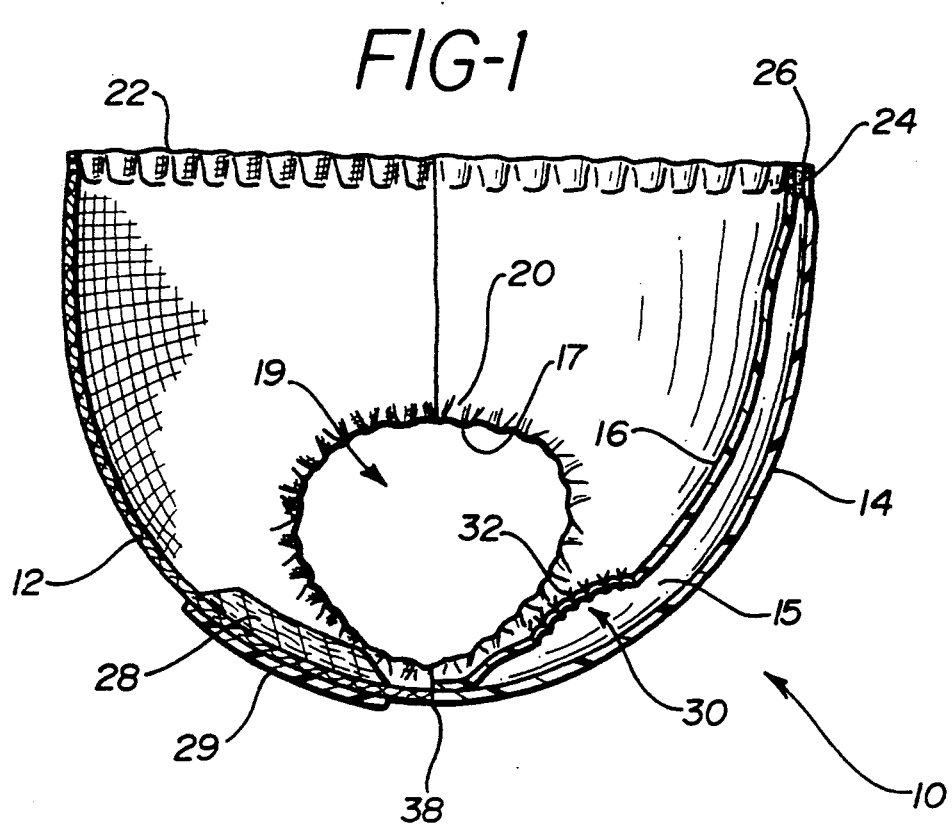
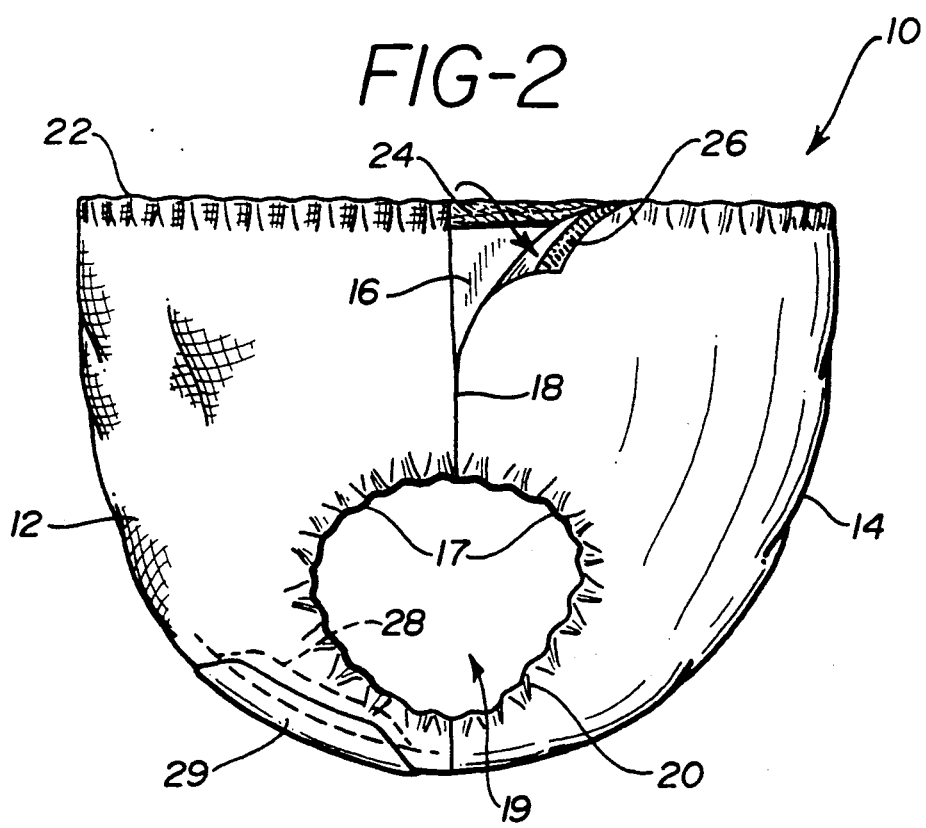

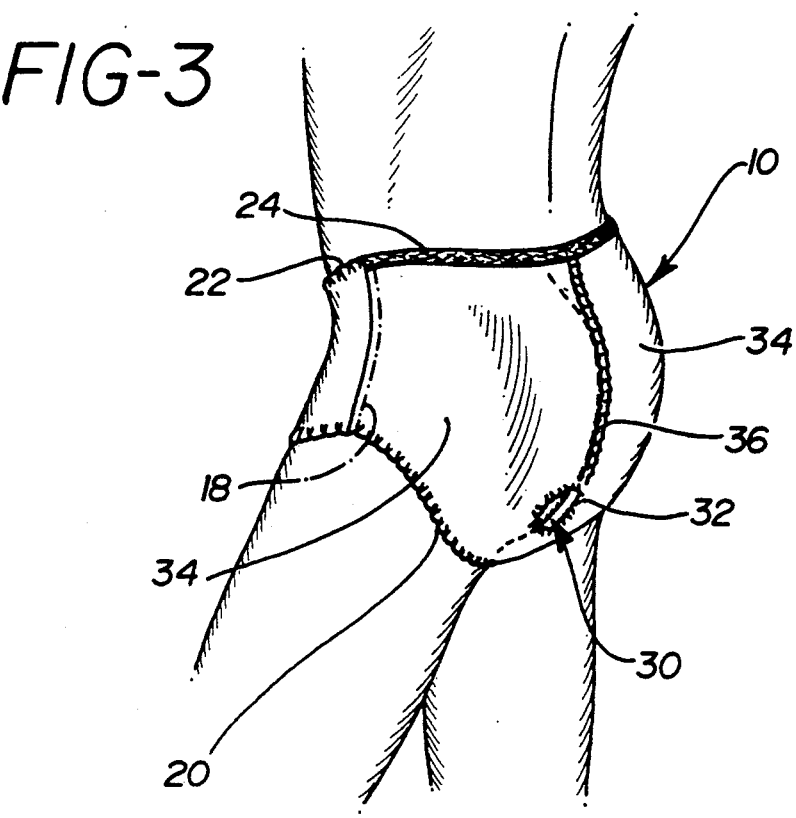
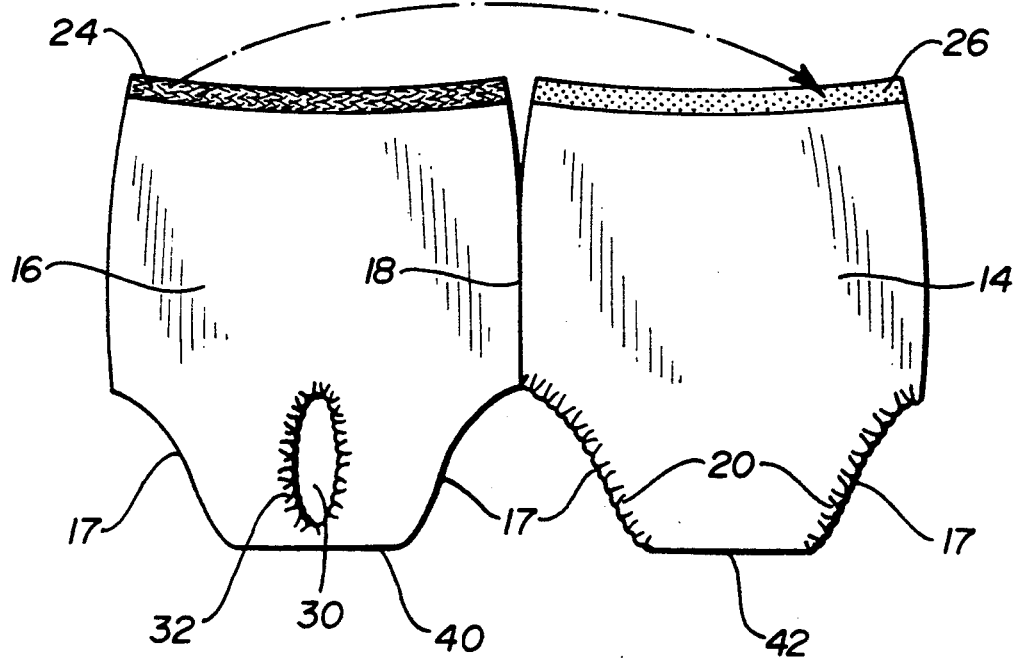

URINARY AND BOWEL INCONTINENCY CONTROL UNDERGARMENT

This is a continuation of application Ser. No. 695,166, filed May 3, 1991, abandoned Feb. 18, 1992.

BACKGROUND OF THE INVENTION

1. Field of the Invention

The present invention relates to the field of incontinent undergarments suitable for wearing by males and females. More specifically, it relates to an improved method for collecting fecal matter directly from the anus of a person.

2. Description of the Prior Art

Numerous forms of incontinence pants or undergarments have hitherto been proposed for the purpose of retaining discharged body fluids. Currently, however, although certain products are known that are somewhat effective for urinary incontinence, most bowel incontinence appliances are so ineffective as to be essentially useless. Efforts to adapt existing infant garments, such as diapers, have not been satisfactory because such garments do not meet the requirements of adults or grown children. Adult clothing is considerably more expensive than that of children, and soiling with escaped body wastes is more distasteful, embarrassing, and expensive to the adult than to the child. In addition, infants are usually confined to cribs having reasonably waterproof bedding during sleeping and, thus, prevention of soiling is more easily accomplished.

Several patents which address this problem describe the adhesive attachment of some form of receptacle directly to the anus of the individual. Examples of this technique are illustrated in U.S. Pat. No. 3,522,807 (Millenbach), U.S Pat. No. 4,445,898 (Jensen), and U.S. Pat. No. 4,784,656 (Christian). A variation on this type of device is a receptacle that is actually inserted into the rectum as disclosed in U.S. Pat. No. 3,548,828 (Vasile). Problems these receptacles include unintentional detachment and discomfort to the patient during use, coupled with the possibility of the formation and accumulation of gas within such collection receptacles. In addition, because of the necessity for continuously unsticking the adhered receptacle from the skin of the wearer, such prior art methods tend to lead to excess skin irritation. Devices with adhesive-coated attachment rings can also be alternatively difficult to affix and adhesion may be difficult to maintain.

Another technique for dealing with bowel incontinence involves various methods of containing the body waste material within the pants or diaper while failing to protect the body skin from contact with the waste material. Such techniques can lead to serious sanitary problems, particularly in women where it is desirable to prevent any fecal material from entering the vagina. Examples of such prior art products include U.S. Pat. Nos. 3,162,196 (Salk), U.S. Pat. No. 3,322,122 (Daniel), U.S. Pat. No. 4,695,279 (Steer), and U.S. Pat. No. 4,753,646 (Enloe).

Many persons who suffer from bowel and/or urinary incontinency are forced to resort to such prior art techniques or to makeshift applications of multiple feminine hygiene products such as sanitary napkins, covered with diapers, tissue, undergarments, or rubber pants. These techniques and makeshift devices are usually ineffective, and in particular, still permit odors to escape and leakage to occur. For this reason, many otherwise healthy and able incontinent persons are forced to remain at home, or are forced into a strict regimen of fasting and careful control of their activities outside the home.

Because of the sensitivity of bowel incontinence in particular, this problem has not previously been adequately addressed by the hygienic protection industry. Thus, there exists a continued need for an effective bowel incontinency control undergarment.

SUMMARY OF THE INVENTION

The product of this invention relates to a pair of unitized pants provided with a double-panel pouch that is designed to be suspended from a waistband and drawn between the buttocks. Providing an elasticized slit or slightly elliptical opening in the inner panel of the pouch permits the admission of body wastes to the pouch directly from the anus. The pant is suspended from the body and operates in conjunction with body movement. Sealing the edges of the garment and lining the pouch with a moisture and odor resistive material, effectively contains body wastes.

Accordingly, it is an object of the present invention to provide an incontinency undergarment to collect fecal material and to prevent excessive contact between the fecal material and the buttocks or other body surfaces. Other and further objects and advantages will appear hereinafter.

While certain apparati have been described utilizing openings leading to collection areas, none of these articles embody the design or advantages of the present invention. See, e.g., European Patent Application No. 0359410A1 (Freeland) and U.S. Pat. No. 4,200,102 (Duhamel et al.). Such articles fail to combine the elastic suspension and locating system of the present invention with a potentially reusable unitized undergarment.

BRIEF DESCRIPTION OF THE DRAWINGS

FIG. 1 is a side cross-sectional view of an embodiment of the present invention.

FIG. 2 is a full side view of the embodiment depicted in FIG. 1.

FIG. 3 is a left rear exploded view of an embodiment of the present invention, as it would be worn by an individual, with its rear outer panel removed.

FIG. 4 is an illustration of a portion of an embodiment of the present invention opened for illustration purposes.

DETAILED DESCRIPTION OF THE PREFERRED EMBODIMENTS

The drawings illustrate various aspects of preferred embodiments of the products of this invention. In the Figures, like numbers designate like elements. An undergarment 10 is generally formed by use of a front panel 12 and a rear panel 14, attached by seams or other attachment means so as to form a panty. The panels are attached so as to form two leg openings 19 surrounded by leg elastic 20. The rear panel 14 is preferably manufactured from a feces-impervious material that is also, preferably, urine-impervious. The front panel 12 can be constructed of any standard garment material. In an alternative embodiment, the entire panty normally formed by front panel 12 and rear panel 14 is constructed of a single piece of material, in which case the entire panty should be urine- and feces-impervious.

In one preferred embodiment of the present invention, the rear panel is constructed of a softer, permeable material bonded to an impervious material, the impervious material being oriented towards the inside of the panty.

An inner panel 16, may typically be constructed of the same material as rear panel 14, and have a similar shape to rear panel 14 is located on the inside of the panty. FIG. 4 illustrates rear panel 14 and inner panel 16 prior to final construction of the undergarment. The inner panel 16 will be attached to rear panel 14 at two side seams 18, only one being illustrated in FIG. 4. In addition, rear inner panel bottom 40 is attached to rear outer panel bottom 42 to form a bottom seam 38 and similar leg portions 17 of the inner panel 16 are attached to corresponding leg portions 17 of the rear panel 14.

Rear panel 14 preferably includes leg elastic 20 along leg portions 17. While such leg elastic 20 can be included along leg portions 17 of the inner panel 16, additional leg elastic 20 is unnecessary. Alternatively, leg elastic 20 can be attached solely to inner panel 16. Once rear panel 14 is fully attached to inner panel 16, the leg elastic 20 will perform its elasticizing function as to both panels regardless of which panel it is initially attached to.

The inner panel 16 includes a slit 30 surrounded by slit elastic 32. The slit 30 is preferably oriented generally perpendicularly to the top of the inner panel 16 at a location near the bottom of the inner panel 16. In one preferred embodiment, the slit elastic 32 is attached to the inner panel 16 such that the slit 30 is formed into an oval or elliptical shape. The slit aperture can be made either by simply cutting vertically through the inner panel 16 or by removing a small portion of the inner panel 16.

Once the inner panel 16 is attached to the rear panel 14, a pouch 15 is formed between the rear panel 14 and the inner panel 16. The pouch 15 is initially open along the top of the undergarment 10. In use, however, a means for closing the top of this pouch 15 is preferable. In a preferred embodiment, a fuzzy elastic strip 24 of a hook and loop fastener, such as VELCRO is attached along the top of the inner panel 16 while a mating strip of a hook and loop fastener 26, such as a VELCRO ™ strip, may be attached along the top of rear panel 14. Strip 26 may act in combination with the elastic strip 24 to seal pouch 15. The use of a fuzzy elastic strip 24 enables the undergarment to be stretched and pulled on over the hips of the wearer and, thereafter, cause the garment to conform elastically to the waist size of that wearer.

In operation, the undergarment 10 should be worn by a bowel-incontinent individual with the rear panel 14 positioned over his or her posterior. The conformation of the undergarment 10 and its elastic components generally position slit 30 in an area adjacent to the anus of the individual. The elastic nature of the leg openings 19, the elastic strip 24, and the slit elastic 32 serve to facilitate and maintain the proper positioning of the slit 30 adjacent to the individual's anus.

In one preferred embodiment, a front waist elastic 22 attached along the top of front panel 12 assists this positioning. Still further, a rear center elastic seam 36, preferably extending from the top of the inner panel 16 down to the slit 30, as illustrated in FIG. 3, assists in drawing the inner panel 16 and the slit 30 between the buttocks of the individual. When undergarment 10 contains such a rear center elastic seam 36 inner, panel 16 can actually be formed from two similar rear inner panels 34 connected by means of the rear center elastic seam 36.

Once undergarment 10 is properly positioned on the individual, any fecal material expelled by the individual will pass directly through the slit 30 and into pouch 15, generally avoiding all contact between such fecal material and the skin of the individual except for minimal soiling of the anal area itself. For women, the fecal material is advantageously prevented from entering the vaginal area, thus reducing risk of vaginal infection.

Thus, the unitized pants of the present invention provides a manner in which the suffering of bowel incontinent persons may be alleviated. Since the edges of the pouch are sealed and the panels are moisture, and preferably odor, resistant, the fecal material is effectively contained. Once soiled, the pouch 15 may be opened by use of the strip 26 and the contents disposed of. Undergarment 10 may then be washed and reused provided that the undergarment 10 is constructed of appropriate materials. Alternatively, the entire undergarment 10 can be disposed of along with the contents of the pouch 15.

In certain embodiments, a urinary incontinence device may be incorporated into the crotch portion of the garment to provide complete protection. In such embodiments, a urinary pad 28 is typically attached or adhered to the crotch portion of the undergarment 10 as illustrated in FIGS. 1 and 2. In addition, a front urine-impermeable panel 29 would preferably be located in the crotch region to which the urinary pad 28 is attached for further protection against unwanted leakage.

In certain embodiments, it is envisioned (although not illustrated herein) that small packets of absorbent material and/or small packets of impregnated sponges of deodorant material may be placed within the pouch 15. An alternative embodiment involves coating the inside of the pouch 15 with a deodorant material. A modular system is preferable since this permits the individual to adjust the performance of the garment to suit his or her needs. Thus, one of the advantages of the present invention is that it provides a means for controlling the odor from bowel incontinence. Since the deodorants will be used within the pouch 15 and, therefore, will not be in direct contact with the individual's skin, entire classes of more effective and powerful, but more irritating, deodorants can be used.

In another embodiment of the present invention, a baby product or diaper utilizing the same elastic suspension system and access slit 30, but in the form of a diaper would be provided. Conventional diapers for infants have included soft cloth material or other absorbent materials that absorb and retain body discharges. During the period between the body discharge and the removal of the diaper, the skin of the infant is in contact with the body discharge. When infant body discharges occur during sleep, the diaper may not be changed for a substantial period of time. During this time, the tender skin of the infant is in continuous contact with the body discharge and may react undesirably to the discharge fluid or fecal matter. Problems of leakage and outer garment staining can also result. The garment of the present invention, however, can be readily adapted for use with infants to overcome these problems simply by adjusting the overall size of the undergarment 10 and assuring that a urinary pad 28 is utilized.

In addition, the undergarment 10 of the present invention can be modified to include non-permanent attachment means along side seams 18. Such non-permanent attachment means would allow for the opening of the undergarment thereby making it easier to put the undergarment on and to later remove it.

With respect to the dimensioning of the slit 30, it has been found that the undergarment 10 performs better if the slit is opened approximately a ¼ of an inch when being worn by the individual. Preferably, the slit should open between about 0.2 and 0.5 inch in use. Thus it is preferable that the slit be formed to accomplish such opening. The slit, even if originally produced by a straight cut or line of opening in the inner panel 16 can be formed as an oval or ellipse by attaching elastic strips to the inner panel 16 in an appropriate manner such that the elastic forms the material of the inner panel 16 into such a shape. Of course, alternative openings and shapes will also be seen to readily accomplish the desired results of the present invention and are intended to be included within the scope of the present invention.

Excessive opening of the slit 30, however, should be avoided because such excessive opening would act to defeat the intended purpose of segregating the fecal material from the individual's skin. In this regard, it has been found that the full rear center elastic seam 36 provides a more effective undergarment in that it accentuates the proper placement and opening of the slit 30 in relationship to the anus. Economic considerations, however, may affect the ultimate design choice.

Thus, a bowel incontinency control undergarment is disclosed that employs an elastically suspended pouch located substantially adjacent to the wearer's anus. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A reusable protective incontinence undergarment comprising:
    a front fabric panel having a top, a bottom, and two sides, the bottom of said front panel separated from each of the two sides by front panel elasticized leg panel portions;
    a rear feces-impervious panel having a top, a bottom, and two sides, the bottom of the rear panel separated from each of the two sides of the rear panel by rear panel elasticized leg panel portions and wherein the bottom of the rear impervious panel is permanently attached to the bottom of the front panel and the two sides of the rear impervious panel are permanently attached to the two sides of the front panel so as to form a panty having two leg openings surrounded by said elasticized leg panel portions of the rear panel;
    an inner feces-impervious panel having a top, a bottom, and two sides, the bottom of the inner panel separated from each of the two sides of the inner panel by leg panel portions and wherein the inner panel has a substantially similar shape to said rear impervious panel and wherein said inner panel sides, leg panel portions and bottom are substantially sealed to said rear impervious panel at said rear panel sides, leg panel portions and bottom, respectively, so as to create a feces-impervious pouch therebetween as an integral part of the panty;
    a slit in the inner panel oriented perpendicularly to the top of the inner panel and located such that the slit is approximately adjacent to an anus of an individual when said undergarment is worn; and
    means for releasably attaching and detaching the tops of the rear panel and inner panel from each other so as to allow access to said pouch when said tops are detached and so as to seal said pouch when said tops are attached.

2. The protective undergarment of claim 1 wherein the means for releasably attaching and detaching the tops of the rear panel and the inner panel comprises a first hook or loop fastener strip attached to the top of one of said inner panel or rear panel and a second respective corresponding, mating loop or hook fastener strip attached to the top of the other of said inner panel or rear panel.

3. The protective undergarment of claim 1 further comprising a urinary pad attached to said front panel and disposed forwardly from said pouch to receive urinary discharge from an individual.

4. The protective undergarment of claim 1 further comprising an elastic seam extending from the top of the inner panel downwardly to the slit.

5. The protective undergarment of claim 1 wherein the top of the front panel is elasticized.

6. The protective undergarment of claim 1 further comprising a deodorant material contained within the pouch.

7. The protective undergarment of claim 1 wherein the slit is an aperture formed by an opening in the inner pane that is elasticized into an oval or elliptical shape.

8. The protective undergarment of claim 1 wherein the slit is about 0.2 inches to about 0.5 inches in width when the panty is worn by an individual.

9. A diaper for the separate collection of urine and fecal matter comprising:
    a front fabric panel having a top, a bottom, and two sides, the bottom of said front panel separated from each of the two sides by front panel elasticized leg panel portions;
    a rear feces-impervious panel having a top, a bottom, and two sides, the bottom of the rear panel separated from each of the two sides of the rear panel by rear panel elasticized leg panel portions and wherein the bottom of the rear impervious panel is attached to the bottom of the front panel along a bottom seam and the two sides of the rear impervious panel are attachable to the two sides of the front panel so as to form a panty having two leg openings surrounded by said elasticized leg panel portions of the front panel and said elasticized leg panel portions of the rear panel;
    an inner feces-impervious panel having a top, a bottom, and two sides, the bottom of the inner panel separated from each of the two sides of the inner panel by leg panel portions and wherein the inner panel has a substantially similar shape to said rear impervious panel and wherein said inner panel sides, leg panel portions and bottom are substantially sealed to said rear impervious panel at said rear panel sides, leg panel portions and bottom, respectively, so as to create an enclosed feces-impervious pouch therebetween, the entirety of said pouch disposed rearwardly from said bottom seam;
    a urinary pad attached to said front panel to receive urinary discharge;
    a slit in the inner panel oriented perpendicularly to the top of the inner panel located such that the slit is approximately adjacent to an anus of an individual or baby when said diaper is worn;

a first hook or loop fastener elastic strip attached to the top of one of said inner or rear panels; and a second respective corresponding, mating loop or hook fastener strip attached to the top of the other of said inner or rear panels, thereby providing means for accessing said pouch for cleaning.

10. The diaper of claim 9 further comprising an elastic seam extending from the top of the inner panel downwardly to the slit.

11. The diaper of claim 9 further comprising a deodorant material contained within the pouch.

12. The diaper of claim 9 wherein the two sides of the rear impervious panel are permanently attached to the two sides of the front panel so as to form a unitary panty.

13. A protective undergarment comprising: a preformed panty having a front portion, a rear portion, a top elasticized opening, and two elasticized leg openings and being constructed of urine and feces impervious material;

an inner feces impervious panel having a top, a bottom, and two sides, the bottom of the inner panel separated from each of the two sides of the inner panel by a leg panel portion and wherein the inner panel has a substantially similar shape to said rear portion of the panty and is substantially sealed to said panty at each similar side, at each similar leg portion and at the bottom so as to create a feces-impervious pouch therebetween;

an elasticized slit in the inner panel oriented perpendicularly to the top of the inner panel and located such that the slit is approximately adjacent to an anus of an individual when said panty is worn by said individual; and means for releasably attaching and detaching the top of the inner panel from the rear portion of the panty top, so as to allow access to said pouch when said tops are detached and so as to seal said pouch when said tops are attached.

14. The protective undergarment of claim 13 wherein the means for attaching and detaching the top of the inner panel to the rear portion of the panty top comprises a first hook or loop fastener elastic strip attached to the top of one of said inner panel or said rear portion of the panty and a second respective corresponding mating loop or hook fastener strip attached to the top of the other of said inner panel or panty.

15. The protective undergarment of claim 13 further comprising a urinary pad attached to said panty front portion to receive urinary discharge from the individual.

16. The protective undergarment of claim 13 further comprising an elastic seam extending from the top of the inner panel downwardly to the slit.

17. The protective undergarment of claim 13 further comprising a deodorant material contained within the pouch.

18. The protective undergarment of claim 13 wherein the slit is an aperture formed by an opening in the inner panel that is elasticized into an oval or elliptical shape.

19. The protective undergarment of claim 13 wherein the slit is about 0.2 inches to about 0.5 inches in width when worn.

20. A reusable protective undergarment comprising:

a front fabric panel having an elasticized top, a bottom, and two sides, the bottom separated from each of the two sides by front panel elasticized leg panel portions;

a rear feces-impervious panel having a top, a bottom, and two sides, the bottom of the rear panel separated from each of the two sides of the rear panel by rear panel elasticized leg panel portions and wherein the bottom of the rear impervious panel is permanently attached to the bottom of the front panel and the two sides of the rear impervious panel are permanently attached to the two sides of the front panel so as to form a panty having two leg openings surrounded by said elasticized leg panel portions of the front panel and said elasticized leg panel portions of the rear panel;

an inner feces impervious panel having a top, a bottom, and two sides, the bottom of the inner panel separated from each of the two sides of the inner panel by leg panel portions and wherein the inner panel has a substantially similar shape to said rear impervious panel and wherein said inner panel sides, leg panel portions and bottom are substantially sealed to said rear impervious panel at said rear panel sides, leg panel portions and bottom, respectively, so as to create a feces impervious pouch therebetween;

a deodorant material contained within the pouch; a urinary pad attached to said undergarment to receive urinary discharge;

an elasticized aperture about 0.2 inches to about 0.5 inches in width in the inner panel oriented perpendicularly to the top of the inner panel located such that the aperture is approximately adjacent to an anus of an individual when said undergarment is worn by said individual and wherein the aperture is formed by an opening in the inner panel that is elasticized into an oval or elliptical shape;

an elastic seam extending from the top of the inner panel downwardly to the slit;

a first hook or loop fastener elastic strip attached to the top of one of said inner panel or rear panel; and a second, respective corresponding, mating loop or hook fastener strip attached to the top of the other of said inner panel or rear panel.

21. The protective undergarment of claim 2 further comprising means for elastically suspending said top of said inner panel from said top of said rear panel.

22. The protective undergarment of claim 21 wherein said elastically suspending means comprises said first hook or loop fastener being an elastic strip.

23. The protective undergarment of claim 1 wherein said inner panel bottom is sealed to said rear panel bottom so as to form a bottom seam defining a forward-most extent of said pouch.

24. The protective undergarment of claim 23 further comprising a urine absorbent pad attached to said front panel and separated from said pouch by said bottom seam.

25. The diaper of claim 9 wherein said urinary pad is disposed entirely forward of said bottom seam.

26. The diaper of claim 9 further comprising an elastic strip affixed to and surrounding a periphery of said slit so that said slit forms an approximately oval shape.

27. The diaper of claim 9 wherein said inner panel is urine impervious.

* * * * *